US009801803B2

(12) United States Patent
Zhou et al.

(10) Patent No.: US 9,801,803 B2
(45) Date of Patent: Oct. 31, 2017

(54) FAST CURING COSMETIC COMPOSITIONS FOR TACK FREE SURFACE PHOTOCURING OF RADICALLY POLYMERIZABLE RESINS WITH UV-LED

(75) Inventors: XianZhi Zhou, Millburn, NJ (US); Chunhua Li, Hillsborough, NJ (US); Hy Si Bui, Piscataway, NJ (US); Jean-Thierry Simonnet, Rueil Malmaison (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/405,470

(22) PCT Filed: Jun. 4, 2012

(86) PCT No.: PCT/US2012/040724
§ 371 (c)(1),
(2), (4) Date: Dec. 4, 2014

(87) PCT Pub. No.: WO2013/184090
PCT Pub. Date: Dec. 12, 2013

(65) Prior Publication Data
US 2015/0139924 A1 May 21, 2015

(51) Int. Cl.
*A61K 8/81* (2006.01)
*A61Q 3/02* (2006.01)
*A61K 8/35* (2006.01)
*A61K 8/55* (2006.01)

(52) U.S. Cl.
CPC ............. *A61K 8/8164* (2013.01); *A61K 8/35* (2013.01); *A61K 8/55* (2013.01); *A61K 8/8152* (2013.01); *A61Q 3/02* (2013.01); *A61K 2800/81* (2013.01); *A61K 2800/95* (2013.01)

(58) Field of Classification Search
CPC ................................. A61K 8/8164; A61Q 3/02
See application file for complete search history.

(56) References Cited

U.S. PATENT DOCUMENTS

| 4,324,744 A | 4/1982 | Lechtken et al. |
| 4,737,593 A | 4/1988 | Ellrich et al. |
| 5,534,559 A | 7/1996 | Leppard et al. |
| 5,785,958 A | 7/1998 | Sirdesai et al. |
| 5,942,290 A | 8/1999 | Leppard et al. |
| 5,965,147 A | 10/1999 | Steffier |
| 6,015,549 A | 1/2000 | Cowperthwaite et al. |
| 6,020,528 A | 2/2000 | Leppard et al. |
| 6,048,660 A | 4/2000 | Leppard et al. |
| 6,244,274 B1 | 6/2001 | Sirdesai et al. |
| 6,391,938 B1 | 5/2002 | Lilley |
| 6,486,226 B2 | 11/2002 | Al-Akhdar et al. |
| 6,486,228 B2 | 11/2002 | Kohler et al. |
| 6,596,445 B1 | 7/2003 | Matsumoto et al. |
| 6,803,394 B2 | 10/2004 | Lilley et al. |
| 6,818,207 B1 | 11/2004 | Schoon et al. |
| 7,081,485 B2 * | 7/2006 | Suh ........................ A61K 6/0017 522/186 |
| 2004/0170924 A1 | 9/2004 | Kunimoto et al. |
| 2005/0234145 A1 | 10/2005 | Sitzmann et al. |
| 2010/0008876 A1 * | 1/2010 | Tanaka ....................... A45D 31/00 424/61 |
| 2010/0160475 A1 | 6/2010 | Stizmann et al. |
| 2010/0236564 A1 | 9/2010 | Ilekti |
| 2011/0060065 A1 | 3/2011 | Vu et al. |
| 2011/0081306 A1 | 4/2011 | Vu et al. |
| 2011/0182837 A1 | 7/2011 | Steffier |
| 2011/0182838 A1 | 7/2011 | Vu et al. |
| 2011/0226271 A1 | 9/2011 | Raney et al. |
| 2011/0256080 A1 | 10/2011 | Kozachek et al. |
| 2011/0274633 A1 | 11/2011 | Vu et al. |

FOREIGN PATENT DOCUMENTS

| JP | 2010-105967 A | 5/2010 |
| WO | 98/33761 A1 | 8/1998 |
| WO | 01/43579 A1 | 6/2001 |
| WO | 2005/100408 A1 | 10/2005 |

OTHER PUBLICATIONS

Ciba Photoinitiators for UV Curing, Key products selection guide 2003, (Oct. 2003), Ciba Specialy Chemicals.*
Extended European Search Report for counterpart EP Application No. 12878559, dated Nov. 2, 2015.

* cited by examiner

*Primary Examiner* — Gina Justice
(74) *Attorney, Agent, or Firm* — The Marbury Law Group, PLLC

(57) ABSTRACT

Disclosed herein are cosmetic compositions comprising (a) at least one ethylenically unsaturated polymerizable compound and (b) at least one photoinitiator system comprising at least one photoinitiator having at least one absorption wavelength greater than about 350 nm. Also disclosed herein are methods of making up and/or enhancing the appearance of a keratinous substrate comprising (1) forming at least one film on the keratinous substrate by applying said cosmetic composition to the keratinous substrate and (2) exposing the film to UV-LED radiation.

21 Claims, No Drawings

FAST CURING COSMETIC COMPOSITIONS FOR TACK FREE SURFACE PHOTOCURING OF RADICALLY POLYMERIZABLE RESINS WITH UV-LED

CROSS REFERENCE TO RELATED APPLICATIONS

This is a national stage application of PCT/US2012/040724, filed internationally on Jun. 4, 2012, which is incorporated herein by reference in its entirety.

FIELD OF THE DISCLOSURE

The disclosure relates to cosmetic compositions comprising (1) at least one ethylenically unsaturated polymerizable compound, and (2) at least one photoinitiator system. In one embodiment, the at least one photoinitiator system comprises at least one photoinitiator having an absorption wavelength greater than about 350 nm. In further embodiments, the photoinitiator having an absorption wavelength greater than about 350 nm is present in an amount of at least about 60%, relative to the total weight of the photoinitiator system. In further embodiments, the photoinitiator system comprises at least two photoinitiators, wherein at least one photoinitiator has at least one absorption wavelength greater than about 350 nm and wherein the total amount of photoinitiators having at least one absorption wavelength greater than about 350 nm is greater than about 60% by weight, relative to the total weight of the photoinitiator system.

In various embodiments, the disclosure relates to systems, compositions, and methods for treating, making up, and/or enhancing the appearance of a keratinous substrate, comprising (1) forming at least one film on the keratinous substrate by applying said cosmetic composition to the keratinous substrate and
(2) exposing the film to UV-LED radiation. The systems, compositions, and methods according to various embodiments of the disclosure may result in relatively thin cosmetic films with a substantially tack-free surface upon photocuring, e.g., with UV-LED, as well as various other improved properties, such as improved shine, adhesion, strength, and/or long wear.

BACKGROUND

Artificial nail and gel-based cosmetic compositions are known. Artificial nails are widely used by women who desire to have long, attractive fingernails that do not break or chip as readily as natural nails. Further, gel-based nail polishes have become increasingly popular in recent years, as they may provide improved properties over conventional nail polishes, such as extended wear and improved shine. However, gel-based nail polishes and compositions for artificial nails are traditionally cured using UV radiation, which may be time-consuming and/or may damage the cosmetic film and/or nail bed.

In recent years, ultra-violet light emitting diodes (UV-LEDs) have been used as an alternative to conventional UV light sources for curing photocurable resins, due to their reduced power consumption and significantly increased lifespan. For instance, the bulbs in UV-LED devices generally do not need to be replaced, making UV-LED devices more cost-efficient. UV-LEDs generally have a single peaked wavelength distribution, for example, at a wavelength ranging from about 380 nm to about 430 nm. In contrast, UV lamps have a peaked distribution at a wavelength ranging from about 250 nm to about 400 nm. The use of UV-LED lamps having a higher wavelength may result in decreased damage to the cosmetic film and/or nail bed relative to that caused mainly by UV light with a shorter wavelength and higher energy.

Further, the use of UV-LED lamps may increase efficiency, for example, by reducing curing time, which thus reduces the amount of time a consumer has to spend having their nails "done." Table 1 below provides a comparison of the time required to cure UV gel-based nail polish, using both UV and UV-LED light sources. As seen in Table 1, gel-based nail polishes can be cured using UV-LED radiation at a significantly reduced curing time. Thus, there is a desire in the cosmetic industry to provide consumers with safer and/or more convenient photocurable cosmetic products that can be cured with UV-LED.

TABLE 1

Exemplary Photocuring Times with UV and UV-LED Light Sources

| Nail Polish Layer | UV light | UV-LED |
|---|---|---|
| Gel Base Coat | 10 sec | 30 sec |
| Gel Color Coat 1 | 2 min | 30 sec |
| Gel Color Coat 2 | 2 min | 30 sec |
| Gel Top Coat | 2 min | 30 sec |
| Total Time | 6 min 10 sec | 2 min |

However, UV-LED is deficient in light with a short wavelength, for example, wavelengths shorter than about 300 nm, or wavelengths shorter than about 350 nm, which may be necessary to reduce oxygen inhibition and achieve suitably cured, i.e., non-tacky, surfaces. Oxygen inhibition occurs when oxygen present in the atmosphere quenches the reactive species produced by photoexcitation at the surface of the film to be cured.

Known nail films cured with UV-LED may therefore present one or more problems, such as defective surface curing and/or undesirable tackiness, leading to an unsatisfactory finished nail appearance and/or feel. To compensate for this deficiency, consumers traditionally apply a thicker coat of polish on the nail bed and, subsequent to curing, remove the tacky layer from the surface to reveal a hard film coating. In addition, U.S. Patent Application Publication No. 2005/234145, incorporated herein by reference in its entirety, discloses a process for photocuring thick layer (e.g., greater than 10 mils) ethylenically unsaturated systems with a LED light source using acylphosphine oxide photoinitiators. However, this process is useful only for thick gel coats, thick multi-ply composites, or thick adhesive layers. Such processes are not useful in the context of thin films, such as the application of a thin cosmetic film to a keratinous substrate, e.g., the nails. Further, U.S. Patent Application Publication No. 2010/160475, incorporated herein by reference in its entirety, discloses processes for photocuring thin layer (e.g., less than 10 mils) ethylenically unsaturated systems using a combination of an acylphoshpine oxide photoinitiator and an acrylated siloxane. However, such processes are time-consuming, requiring extended periods of LED radiation, which, as described above, is not suitable in the context of cosmetic applications. Also, the incorporation of additional components, such as acrylated siloxanes, serves to increase the overall production and consumer costs of such compositions.

Other methods for overcoming the inability of UV-LED to reduce oxygen inhibition have also been considered. For example, amines have been added to compositions that are to be cured using UV-LED. The amines readily undergo a chain peroxidation reaction which consumes oxygen that diffuses into the film. However, the presence of amines in the compositions may present various problems, such as yellowing of the cosmetic film, undesirable odors, plasticizing effects, softening of the cosmetic film coating due to the chain reactions, and/or decreased resistance of the cosmetic film to wear due to the formed hydroperoxides.

Other methods include application of a wax barrier coat or performing the UV-LED exposure under water to slow down the diffusion of atmospheric oxygen into the UV-curable composition. However, such methods may adversely affect the surface properties of the cosmetic film. Further, immersion in water may increase the risk of skin sensitization due to uncured monomers which may be present in the water in trace amounts. Another method involves performing the UV-LED exposure under inert conditions, which effectively overcomes oxygen inhibition, but is not a cost-effective or practical solution for nail enamel application.

Thus, there remains a desire to provide a photocurable cosmetic product that can be cured under UV-LED, which also makes it possible to more safely and/or more conveniently obtain a tack-free cosmetic film. It has now been surprisingly discovered that cosmetic compositions comprising (1) at least one ethylenically unsaturated polymerizable compound, and (2) a photoinitiator system, e.g., comprising (a) at least one photoinitiator having an absorption wavelength greater than about 350 nm, or (b) at least two photoinitiators wherein at least one photoinitiator has at least one absorption wavelength greater than about 350 nm, may yield tack-free, thin cosmetic films upon photocuring with UV-LED radiation, and may also significantly reduce curing times.

DESCRIPTION OF EXEMPLARY EMBODIMENTS

This disclosure relates, in various embodiments, to cosmetic compositions comprising (1) at least one ethylenically unsaturated polymerizable compound and (2) at least one photoinitiator system comprising at least one photoinitiator having an absorption wavelength greater than about 350 nm. In various embodiments, the at least one photoinitiator system comprises at least two photoinitiators, wherein at least one photoinitiator has at least one absorption wavelength greater than about 350 nm. In at least certain embodiments, at least one photoinitiator having at least one absorption wavelength greater than about 350 nm is present in the photoinitiator system in an amount greater than about 60% by weight, relative to the total weight of the photoinitiator system.

Ethylenically Unsaturated Polymerizable Compound

Ethylenically unsaturated polymerizable compounds suitable for use in accordance with the present disclosure may include, for example, compounds having a molecular weight of less than about 10,000 and at least one olefinic double bond. Such compounds may have lower molecular weight, e.g., monomeric compounds, or higher molecular weight, e.g., oligomeric or polymeric compounds having a molecular weight of less than about 10,000. In various embodiments, the at least one ethylenically unsaturated polymerizable compound may have a molecular weight ranging from 100 to about 10,000, for example, from about 200 to about 3,000.

According to various exemplary embodiments of the disclosure, ethylenically unsaturated monomers useful in various embodiments may be mono-, di-, tri-, or polyfunctional with respect to the addition-polymerizable ethylenic bonds. A variety of ethylenically unsaturated compounds are suitable, so long as the compounds are capable of reacting to yield a polymerized artificial nail structure and/or film upon exposure to UV-LED radiation. Suitable ethylenically unsaturated polymerizable compounds are described, for example, in U.S. Patent Application No. 2010/0160475, incorporated herein by reference in its entirety.

In various embodiments, the at least one ethylenically unsaturated compound may be chosen from monomers of general formula (I):

wherein:

$R_1$ is chosen from hydrogen and $C_1$-$C_{30}$ straight or branched chain alkyl, aryl, and aralkyl radicals; and $R_2$ is chosen from pyrrolidones and aromatic, alicyclic, or bicyclic rings optionally substituted with at least one substituent chosen from $C_1$-$C_{30}$ straight or branched chain alkyl radicals; —COOM radicals, wherein M is chosen from hydrogen, $C_1$-$C_{30}$ straight or branched chain alkyl radicals, pyrollidones, and aromatic, alicyclic, and bicyclic rings optionally substituted with at least one substituent chosen from $C_1$-$C_{30}$ straight or branched chain alkyl radicals which may be substituted with at least one hydroxyl group, and $[(CH_2)_mO]_nH$, wherein m is a number ranging from about 1 to about 20 and n is a number ranging from about 1 to about 200.

According to at least one exemplary embodiment, the at least one ethylenically unsaturated polymerizable compound may be chosen from monofunctional monomers of formula (I), wherein $R_1$ is chosen from hydrogen and $C_1$-$C_{30}$ alkyl radicals and $R_2$ is chosen from —COOM radicals, wherein M is chosen from $C_1$-$C_{30}$ straight or branched chain alkyl radicals optionally substituted with at least one hydroxyl group. In another embodiment, the at least one ethylenically unsaturated polymerizable compound may be chosen from monofunctional monomers of formula (I), wherein $R_1$ is chosen from hydrogen and $CH_3$, and $R_2$ is chosen from —COOM radicals, wherein M is chosen from $C_1$-$C_{10}$ straight or branched chain alkyl radicals optionally substituted with at least one hydroxyl group. For example, the monofunctional monomer may be chosen from (meth)acrylate monomers, such as methyl (meth)acrylate (MMA), ethyl (meth)acrylate (EMA), butyl (meth)acrylate (BMA) and tetrahydrofurfuryl methacrylate (THFMA), and hydroxyalkyl (meth)acrylate monomers, such as hydroxypropyl methacrylate (HPMA), hydroxyethyl (meth)acrylate (HEMA), and butoxyethyl (meth)acrylate (BEMA).

In another exemplary embodiment, the monofunctional monomers may be chosen from diethylaminoethyl (meth) acrylate, 2-ethyl-hexyl (meth)acrylate, methoxyethylene glycol(meth)acrylate, methoxypolyethylene glycol(meth) acrylate, phenoxyethylene glycol(meth)acrylate, phenoxypolyethylene glycol(meth)acrylate, 2-hydroxy-3-phenoxypropyl (meth)acrylate, 2-(meth)acryloyloxyethylsuccinic acid, 2-(meth)acryloyloxyethylphthalic acid, 2-(meth)acryloyloxypropylhexahydrophthalic acid, stearyl(meth)acrylate, isobornyl (meth)acrylate, phosphoethyl (meth)acrylate, methoxypropyl (meth)acrylate, and 3-chloro-2-hydroxypropyl (meth)acrylate.

Di-, tri-, and polyfunctional monomers, as well as oligomers and polymers of the monofunctional monomers disclosed herein, are also suitable for use as the at least one ethylenically unsaturated polymerizable compound. Di-, tri-, and polyfunctional monomers may aid in crosslinking of the composition during and after polymerization. According to certain non-limiting embodiments, the at least one ethylenically unsaturated polymerizable compound may be chosen from difunctional monomers of general formula (II):

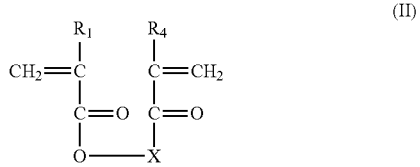

wherein:

$R_3$ and $R_4$ are independently chosen from hydrogen and $C_1$-$C_{30}$ straight or branched chain alkyl, aryl, and aralkyl radicals; and X is chosen from $[(CH_2)_xO_y]_z$ radicals, wherein x is a number ranging from about 1 to about 20, y is a number ranging from about 1 to about 20, and z is a number ranging from about 1 to about 100.

The at least one ethylenically unsaturated polymerizable compound may, for example, be chosen from difunctional monomers of formula (II) wherein $R_3$ and $R_4$ are $CH_3$ radicals and X is chosen from $[(CH_2)_xO_y]_z$ radicals, wherein x is a number ranging from about 1 to about 4, y is a number ranging from about 1 to about 6, and z is a number ranging from about 1 to about 10. In one embodiment, the at least one ethylenically unsaturated polymerizable compound may be chosen from difunctional monomers of formula (II), wherein $R_3$ and $R_4$ are $CH_3$ radicals and X is $[(CH_2)_2O]_4$.

For example, the difunctional monomer may be chosen from 1,4-butanediol di(meth)acrylate, 1,6-hexanediol di(meth)acrylate, 1,9-nonanediol di(meth)acrylate, 1,10-decanediol di(meth)acrylate, neopentyl glycol di(meth)acrylate, 2-methyl-1,8-octanediol di(meth)acrylate, glycerol di(meth)acrylate, polyglycerin di(meth)acrylate, ethylene glycol di(meth)acrylate, polyethylene glycol di(meth)acrylate, propylene glycol di(meth)acrylate, polypropylene glycol di(meth)acrylate, ethoxylated polypropylene glycol di(meth)acrylate, ethoxylated bisphenol A di(meth)acrylate, propoxylated bisphenol A di(meth)acrylate, proposylated ethoxylated bisphenol A di(meth)acrylate, tricyclodecanedimethanol di(meth)acrylate, bis acrylamides, bis allyl ethers, and allyl (meth)acrylates.

Suitable trifunctional and polyfunctional monomers may be chosen, for example, from acrylates and methacrylates and their esters, such as trimethylolpropane tri(meth)acrylate, trimethylolpropane tri(meth)acrylate ester, ethoxylated trimethylolpropane tri(meth)acrylate, ethoxylated glycerin tri(meth)acrylate, ethoxylated isocyanuric acid tri(meth) acrylate, pentaerythritol tri(meth)acrylate, pentaerythritol tetra(meth)acrylate, propoxylated pentaerythritol tetra(meth)acrylate, ethoxylated pentaerythritol tetra(meth)acrylate, ditrimethylolpropane tetra(meth)acrylate, dipentaerythritol penta(meth)acrylate, and dipentaerythritol hexa(meth)acrylate.

According to various embodiments, the at least one ethylenically unsaturated polymerizable compound may be chosen from urethane (meth)acrylates comprising at least two acryl or methacryl groups and a urethane group. Non-limiting examples of such urethane (meth)acrylates include urethanes based on aliphatic, aromatic, polyester, and polyether polyols and aliphatic, aromatic, polyester and polyether diisocyanates capped with (meth)acrylate end groups. Epoxy (meth)acrylates and epoxy urethane (meth) acrylates useful in accordance with the present disclosure may have at least two (meth)acryl groups and, optionally, a urethane group. Non-limiting examples include epoxy (meth)acrylates based on aliphatic or aromatic epoxy prepolymers capped with (meth)acrylate end groups. Optionally, an aliphatic or aromatic urethane spacer may be inserted between the epoxy and the (meth)acrylate end groups. In a further exemplary embodiment, the at least one ethylenically unsaturated polymerizable compound may be chosen from acrylated polyester oligomers comprising at least two (meth)acryl groups and a polyester core; acrylated polyether oligomers comprising at least two (meth)acryl groups and a polyether core; and acrylated acrylate oligomers comprising at least two (meth)acryl groups and a polyacrylic core. Such reactive urethanes, epoxies, polyesters, polyethers, and acrylics are available from several suppliers including, but not limited to BASF Corporation, Bayer MaterialScience AG, Bomar Specialties Co., Cognis Corporation, DSM NeoResins, Eternal Chemical Co., Ltd., IGM Resins, Rahn AG, Sartomer USA, LLC, and SI Group, Inc.

By way of further non-limiting example, ethylenically unsaturated polymerizable compounds also include those described in U.S. Pat. Nos. 5,785,958, 5,965,147, 6,015,549, 6,244,274, 6,391,938, 6,803,394, and 6,818,207; U.S. Patent Application Publication Nos. 2011/060065, 2011/081306, 2011/182838, and 2011/274633; and U.S. Provisional Patent Application Nos. 61/476,337, 61/476,338, 61/476,339, 61/476,340, and 61/476,341, the disclosures of which are incorporated herein by reference in their entireties.

According to various exemplary embodiments, the at least one ethylenically unsaturated polymerizable compound may be chosen from modified epoxy acrylates or polymeric tetrafunctional acrylates. Exemplary commercial ethylenically unsaturated polymerizable products that may be used in accordance with the disclosure include, but are not limited to, products sold by BASF under the trade name LAROMER™ and products sold by Bayer MaterialScience AG under the trade name DESMOLUX™.

In various exemplary embodiments, the at least one ethylenically unsaturated polymerizable compound may be present in the cosmetic composition in an amount greater than about 5% by weight, such as an amount ranging from about 10% to about 99% by weight, from about 20% to about 95% by weight, from about 30% to about 90% by weight, or from about 40% to about 75% by weight, relative to the total weight of the cosmetic composition.

Photoinitiator System

As described herein, the cosmetic composition comprises at least one photoinitiator system comprising, in various exemplary embodiments, at least one photoinitiator having at least one absorption wavelength greater than about 350 nm. In various embodiments, the at least one photoinitiator is present in an amount greater than about 60% by weight of the photoinitiator system.

In further embodiments, the photoinitiator system comprises at least two photoinitiators, wherein at least one photoinitiator has at least one absorption wavelength greater than about 350 nm. In various embodiments where the photoinitiator system comprises at least two photoinitiators, the total amount of photoinitiators having at least one absorption wavelength greater than about 350 nm is greater than about 60% by weight, relative to the total weight of the photoinitiator system. In certain embodiments, the at least one photoinitiator system may comprise at least one photoinitiator that is active at longer UV wavelengths and/or visible light wavelengths.

The at least one photoinitiator may exhibit at least one absorption peak at a wavelength greater than about 350 nm, such as greater than about 360 nm, greater than about 370 nm, greater than about 380 nm, or greater than about 390 nm. Alternatively, the at least one photoinitiator may be active at visible light wavelengths, e.g., wavelengths greater than about 400 nm, for instance, wavelengths ranging from about 400 nm to about 800 nm.

According to various embodiments of the disclosure, the at least one photoinitiator having at least one absorption wavelength greater than about 350 nm may be chosen from monoacylphosphine oxides and bisacylphosphine oxides, red-shifted phenylglyoxylates, red-shifted benzophenones, and isoproylthioxanthones having at least one absorption wavelength greater than about 350 nm. Exemplary mono- and bisacylphosophine oxide photoinitiators suitable for use in accordance with the present invention are disclosed, for example, in U.S. Pat. Nos. 4,324,744, 4,737,593, 5,942,290, 5,534,559, 6,020,528, 6,486,226, and 6,486,228, the disclosures of which are incorporated herein by reference in their entireties.

By way of non-limiting example only, suitable monoa-cylphosphine oxides may be chosen from compounds of general formula (III):

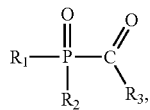

(III)

wherein:

$R_1$ is chosen from $C_1$-$C_{12}$ alkyl, benzyl, and phenyl radicals optionally substituted with at least one substituent chosen from halogens and $C_1$-$C_8$ alkyl and alkoxy radicals; cyclohexyl radicals; and —$OR_4$ radicals, wherein $R_4$ is chosen from $C_1$-$C_8$ alkyl, phenyl, and benzyl radicals;

$R_2$ is chosen from $C_1$-$C_{12}$ alkyl, benzyl, and phenyl radicals optionally substituted with at least one substituent chosen from halogens and $C_1$-$C_8$ alkyl and alkoxy radicals; and cyclohexyl radicals; and $R_3$ is chosen from phenyl radicals optionally substituted with at least one substituent chosen from halogens and $C_1$-$C_8$ alkyl, alkoxy, and alkylthio radicals.

For example, in at least one embodiment, $R_1$ may be chosen from —$OR_4$ and phenyl radicals, $R_2$ may be chosen from phenyl radicals optionally substituted with at least one substituent chosen from halogens and $C_1$-$C_8$ alkyl and alkoxy radicals, and $R_3$ may be chosen from phenyl groups optionally substituted with at least one $C_1$-$C_8$ alkyl radical. In another embodiment, $R_1$ and $R_2$ are phenyl groups. According to at least one exemplary embodiment, the monoacylphosphine oxide is chosen from 2,4,6-trimethyl-benzoylethoxyphenylphosphine oxide and 2,4,6-trimethyl-benzoyldiphenylphosphine oxide.

Non-limiting examples of suitable bisacylphosphine oxides include those of general formula (IV):

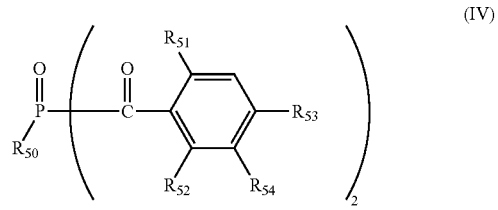

wherein:

$R_{50}$ is chosen from $C_1$-$C_{12}$ alkyl, cyclohexyl, and phenyl radicals optionally substituted with at least one substituent chosen from halogens and $C_1$-$C_8$ alkyl radicals, $SR_{10}$, and $N(R_{11})(R_{12})$, wherein:

$R_{10}$, $R_{11}$, and $R_{12}$ are independently chose from hydrogen, $C_1$-$C_{24}$ alkyl radicals, $C_2$-$C_{24}$ alkenyl radicals, $C_3$-$C_8$ cycloalkyl radicals, phenyl radicals, benzyl radicals, and $C_2$-$C_{20}$ alkyl radicals interrupted by at least one non-consecutive oxygen atom and optionally substituted by at least one group chosen from —OH and —SH, or $R_{11}$ and $R_{12}$, together with the nitrogen atom to which they are bonded, form a 5- or 6-membered ring, optionally comprising at least one entity chosen from oxygen, sulfur, and $NR_{13}$, wherein $R_{13}$ is chosen from hydrogen, phenyl radicals, $C_1$-$C_{12}$ alkoxy radicals, $C_1$-$C_{12}$ alkyl radicals, and $C_2$-$C_{12}$ alkyl radicals interrupted by at least one non-consecutive oxygen atom and optionally substituted by at least one group chosen from —OH and —SH;

$R_{51}$ and $R_{52}$ are independently chosen from $C_1$-$C_8$ alkyl and alkoxy radicals;

$R_{53}$ is chosen from hydrogen and $C_1$-$C_{10}$ alkyl radicals; and $R_{54}$ is chosen from hydrogen and methyl radicals.

According to various exemplary embodiments, the at least one photoinitiator having at least one absorption wavelength greater than about 350 nm may be chosen from bisacylphosphine oxides of formula (IV), wherein $R_{50}$ is chosen from $C_2$-$C_{10}$ alkyl, cyclohexyl, and phenyl radicals optionally substituted with at least one substituent chosen from $C_1$-$C_4$ alkyl radicals, chlorine, and bromine. In one non-limiting embodiment, $R_{50}$ is chosen from $C_3$-$C_8$ alkyl, cyclohexyl, and phenyl radicals optionally substituted on the 2-, 3-, 4-, or 2,5-positions by a $C_1$-$C_4$ alkyl radical. For example, $R_{50}$ may be chosen from $C_4$-$C_{12}$ alkyl and cyclohexyl radicals, $R_{51}$ and $R_{52}$ may be independently chosen from $C_1$-$C_8$ alkoxy radicals, and $R_{53}$ may be chosen from hydrogen and $C_1$-$C_4$ alkyl groups. In at least one further exemplary embodiment, $R_{51}$ and $R_{52}$ may be independently chosen from methyl and methoxy radicals, and $R_{53}$ may be chosen from hydrogen and methyl radicals. According to yet another exemplary embodiment, the radicals $R_{51}$, $R_{52}$, and $R_{53}$ are methyl radicals. In a further exemplary embodiment, the radicals $R_{51}$, $R_{52}$, and $R_{53}$ are methyl radicals and $R_{54}$ is hydrogen.

For example, $R_{50}$ may be chosen from $C_3$-$C_8$ alkyl radicals. In one exemplary embodiment, $R_{50}$ may be chosen from isobutyl and phenyl radicals. In another exemplary embodiment, $R_{51}$ and $R_{52}$ are methoxy radicals, $R_{53}$ and $R_{54}$ are hydrogen, and $R_{50}$ is an isooctyl radical. According to at least one exemplary embodiment, the bisacylphosphine oxide is chosen from bis(2,4,6-trimethylbenzoyl)-phenyl-phosphine oxide, bis(2,4,6-trimethylbenzoyl)-(2,4-bis-pentyloxyphenyl) phosphine oxide, and bis(2,6-dimethoxybenzoyl)-2,4,4-trimethylpentylphosphine oxide.

According to various exemplary embodiments, the at least one photoinitiator having at least one absorption wavelength greater than about 350 nm is chosen from bis(2,4,6-trimethylbenzyol)-phenyl phosphine oxide and ethyl-2,4,6-trimethylbenzoylphenylphosphinate. Exemplary commercial photoinitiator products having at least one absorption wavelength greater than about 350 nm that may be used in accordance with the disclosure include, but are not limited to, the products sold by BASF Resins under the names IRGACURE® 2100, IRGACURE® 819, and LUCIRIN® TPO-L; the product sold by Cytec Industries, Inc. under the name ADDITOL® TPO; and the product sold by Lamberti under the name ESACURE® TPO.

The at least one photoinitiator system as described herein comprises, in at least certain embodiments, greater than about 60% by weight of at least one photoinitiator having at least one absorption wavelength greater than about 350 nm, relative to the total weight of the photoinitiator system. In further embodiments, the photoinitiator system comprises at least two photoinitiators, wherein at least one photoinitiator has at least one absorption wavelength greater than about 350 nm, wherein the total amount of photoinitiators having at least one wavelength greater than about 350 nm is greater than about 60% by weight, relative to the total weight of the photoinitiator system.

By way of example only, the total amount of the at least one photoinitiator having at least one wavelength greater than about 350 nm may be greater than about 60% by weight, for instance, greater than about 65%, greater than about 70%, greater than about 75%, greater than about 80%, or greater than about 90%, by weight, relative to the total weight of the photoinitiator system. In various exemplary embodiments, the total amount of the at least one photoinitiator having at least one wavelength greater than about 350 nm ranges from about 60% to about 99%, about 65% to about 97%, about 70% to about 95%, or from about 75% to about 90%, by weight, relative to the total weight of the photoinitiator system.

According to various exemplary embodiments, the at least one photoinitiator system may comprise a mixture of at least two photoinitiators having at least one absorption wavelength greater than about 350 nm, wherein the total amount of photoinitiators having at least one absorption wavelength greater than about 350 nm is about 100% by weight, relative to the total weight of the photoinitiator system. For example, the at least one photoinitiator system may comprise a mixture of bis(2,4,6-trimethylbenzoyl)phenylphosphine oxide and 2,4,6-trimethylbenzoylethoxyphenyl-phosphine oxide, wherein the weight ratio of the two photoinitiators is about 4:3, respectively.

In another exemplary embodiment, the at least one photoinitiator system may comprise a mixture of at least one photoinitiator having at least one absorption wavelength greater than about 350 nm and at least one second photoinitiator that does not have an absorption wavelength greater than about 350 nm, wherein the total amount of photoinitiators having at least one absorption wavelength greater than about 350 nm is greater than about 60% by weight, for example, greater than about 65%, greater than about 70%, or greater than about 75% by weight, relative to the total weight of the photoinitiator system. For example, the at least one photoinitiator system may comprise a mixture of at least one first photoinitiator having at least one absorption wavelength greater than about 350 nm and at least one second photoinitiator not having an absorption wavelength greater than about 350 nm, wherein the weight ratio of the first photoinitiator to the second photoinitiator is greater than about 3:2, respectively. For instance, the weight ratio may be greater than about 7:3, or greater than about 3:1.

The at least one second photoinitiator may be chosen, for example, from α-hydroxyketones; α-aminoketones; benzophenones; ketal compounds; monomeric and dimeric phenylglyoxylic acids and their esters; and oxime esters, which do not have an absorption wavelength greater than 350 nm.

By way of non-limiting example, the at least one second photoinitiator may be chosen from α-hydroxyketones, such as 1-hydroxycyclohexylphenylketone, 2-hydroxy-1-[4-(2-hydroxyethoxy)phenyl]-2-methyl-1-propanone, and 2-hydroxy-2-methyl-1-phenyl-1-propanone; α-aminoketones, such as 2-methyl-1-[4-(methylthio)phenyl]-2-(4-morpholinyl)-1-propanone, 2-benzyl-2-(dimethylamino)-1-[4-(4-morpholinyl)phenyl]-1-butanone, 2-(4-methyl-benzyl-2-(dimethylamino)-1-[4-(4-morpholinyl)phenyl]-1-butanone, and 2-benzyl-2-(dimethylamino)-1-[3,4-dimethoxyphenyl]-1-butanone; benzophenones, such as benzophenone, 2,4,6-trimethylbenzophenone, 4-methylbenzophenone, 2-methylbenzophenone, 2-methoxycarbonylbenzophenone, 4,4'-bis(chloromethyl)benzophenone, 4-chlorobenzophenone, 4-phenyl-benzophenone, 4,4'-bis(dimethylamino)benzophenone, 4,4'-bis(diethylamino)benzophenone, methyl 2-benzoylbenzoate, 3,3'-dimethyl-4-methoxybenzophenone, 4-(4-methylphenylthio)-benzophenone, 2,4,6-trimethyl-4'-phenyl-benzophenone, and 3-methyl-4'-phenyl-benzophenone; ketal compounds, for example, 2,2-dimethoxy-1,2-diphenyl-ethanone; and monomeric or dimeric phenylglyoxylic acid esters, such as methylphenylglyoxylic acid ester, 5,5'-oxo-di(ethyleneoxydicarbonylphenyl), and 1,2-(benzoylcarboxy)ethane.

According to various exemplary embodiments, the at least one second photoinitiator may be chosen from oxime esters, for example, the oxime esters disclosed in U.S. Pat. No. 6,596,445 and U.S. Patent Application Publication No. 2004/0170924, the disclosures of which are incorporated herein by reference in their entireties, and the following compounds of formulae (V) and (VI):

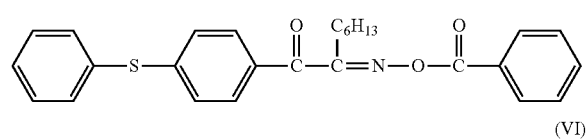

(V)

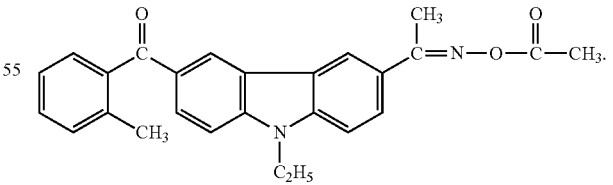

(VI)

In at least one further exemplary embodiment, the at least one second photoinitiator may be chosen from pheynyl glyoxylates, for example, those disclosed in U.S. Pat. No. 6,048,660, the disclosure of which is incorporated herein by reference in its entirety, and phenyl glyoxylates of general formula (VII):

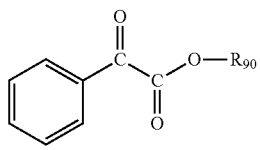

(VII)

wherein $R_{90}$ is chosen from $C_1$-$C_4$ alkyl radicals, for example, methyl radicals, or radicals of formula (VIII):

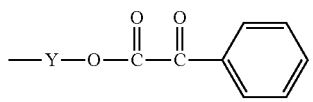

(VIII)

wherein Y is chosen from $C_1$-$C_{12}$ alkylene radicals, cyclohexene radicals, $C_2$-$C_{40}$ alkylene radicals interrupted by at least one entity chosen from cyclohexene, oxygen, sulfur, and $NR_{30}$, wherein $R_{30}$ is chosen from hydrogen, $C_1$-$C_{12}$ alkyl radicals, and phenyl radicals. In at least one embodiment, Y may be $CH_2CH_2OCH_2CH_2$.

According to various exemplary embodiments, the at least one second photoinitiator not having an absorption wavelength greater than 350 nm may be chosen from 1-hydroxycyclohexyl-phenyl-ketone, 2-hydroxy-1-[4-(2-hydroxyethoxyl)phenyl]-2-methyl-1-propanone, and 2-hydroxy-2-methyl-1-phenyl-1-propanone. Exemplary photoinitiators not having an absorption wavelength greater than 350 nm are commercially available, such as the products sold by BASF Resins under the names IRGACURE® 184, IRGACURE® 2959 and DAROCUR® 1173; the product sold by Cytec Industries, Inc. under the name ADDITOL® CPK; and products sold by Lamberti under the names ESACURE® KL 200 and ESACURE® KS 300.

The photoinitiator system may, in certain embodiments, be present in the cosmetic composition in an amount ranging up to about 15% by weight, such as, for example, from about 0.1% to about 10% by weight, from about 0.5% to about 7.5% by weight, or from about 1% to about 5%, relative to the total weight of the composition. By way of non-limiting example only, the at least one photoinitiator having at least one absorption wavelength greater than 350 nm may be present in an amount up to about 7% by weight, such as up to about 5% by weight, such as from about 0.5% to about 6%, from about 1% to about 5%, or from about 2% to about 4%, by weight, relative to the total weight of the composition. Similarly, where present, at least one second photoinitiator, e.g., a photoinitiator not having an absorption wavelength greater than 350 nm, may be present in an amount up to about 7% by weight, such as up to about 5% by weight, such as from about 0.5% to about 6%, from about 1% to about 5%, or from about 1% to about 3%, by weight, relative to the total weight of the composition.

Additional Components

Additional cosmetic ingredients may optionally be included in the cosmetic compositions according to the disclosure. Such ingredients are known, and include, but are not limited to, solvents (including water), colorants, humectants, emulsifiers, surfactants, preservatives, fragrances, thickeners or texturizers, emollients, additional film-formers, coalescents, and/or plasticizers. One of skill in the art will be able to select the appropriate types and amounts of additional cosmetic ingredients, based on, for example, the type of cosmetic composition being formulated and the desired properties thereof. By way of example only, such additional cosmetic ingredients may be present in the compositions according to the disclosure in a combined amount up to about 95% by weight, such as, for example, an amount ranging from about 5% to about 90% by weight, such as from about 10% to about 80%, from about 20% to about 75%, or from about 25% to about 50%, by weight, relative to the total weight of the composition.

One or more binders may be present in the compositions of the disclosure, for example, when the cosmetic composition is in a liquid or viscous form. The at least one binder may be present in the cosmetic composition in an amount ranging from about 5% to about 95% by weight, for example, from about 10% to about 90%, or from about 40% to about 90%, relative to the total weight of the composition. It is within the ability of a skilled artisan to vary the amount of binder based on the desired cosmetic properties and field of use, such as the ability of the compositions to be developed in aqueous and organic solvent systems, adhesion of the compositions to a substrate, and susceptibility to oxygen.

Suitable binders in accordance with the disclosure may be chosen, for example, from polymers having a molecular weight ranging from about 5,000 to about 2,000,000, for instance, from about 10,000 to about 1,000,000. Non-limiting examples of such polymers include homo- and copolymers of acrylates and methacrylates, such as copolymers of methyl methacrylate/ethyl acrylate/methacrylic acid, poly(alkylmethacrylates), and poly(alkylacrylates); cellulose esters and ethers, such as cellulose acetate, cellulose acetobutyrate, methyl cellulose, and ethyl cellulose; polyvinyl butyral; polyvinyl formal; cyclized rubber; polyethers, such as polyethylene oxide, polypropylene oxide, and polytetrahydrofuran; polystyrene; polycarbonate; polyurethane; chlorinated polyolefins; polyvinyl chloride; copolymers of vinyl chloride/vinylidene chloride; copolymers of vinylidene chloride with acrylonitrile; methyl methacrylate; vinyl acetate; polyvinyl acetate; copoly(ethylene/vinyl acetate); polymers such as polycaprolactam and poly(hexamethylene adipamide); and polyesters such as poly(ethylene glycol terephthalate) and poly(hexamethylene glycol succinate).

In addition, the compositions of the present disclosure may comprise at least one non-photopolymerizable film forming component. Non-limiting examples of suitable film formers include physically drying polymers and solutions thereof in organic solvents, for example, nitrocellulose and cellulose acetobutyrate.

One or more coloring agents and/or pigments may be present in the cosmetic compositions of the disclosure, for example, when it is desired that the composition has a coloring and/or opacifying effect. Pigments suitable for use in accordance with the disclosure include, but are not limited to, D & C red Nos. 10, 11, 12, and 13; D & C red No. 7; and TOB-BON maroon (D & C red No. 34). Other pigments which may be used in compositions according to the present invention include lake pigments, for example, D & C yellow No. 5 Lake, D & C Red No. 2 Lake, and Ext. D & C Red No. 2 Lake. Additional pigments may include cosmetic-grade or purified titanium dioxide (white), yellow and red iron oxides, iron blue, iron black, ultramarine blue, chromide oxide greens, carbon black, and/or lampblack.

In addition to the above-named pigments, iridescent additives may be included, for example, "pearl essence", which is a suspension of crystalline guanine in nitrocellulose and solvents as well as other additives which will affect the appearance of the pigment. Although the amount of pigment in the compositions of the present invention will vary as a function of the type of pigment and other components included in the compositions, in general, the at least one pigment may be present in the composition in an amount ranging from about 0.025% to about 10% by weight, for example, from about 0.5% to about 4% by weight, relative to the total weight of the composition.

Other additives generally present in gel-based and acrylic nail compositions may also be added to the compositions of the disclosure, for example, thermal inhibitors, which may prevent premature polymerization; copper compounds and quaternary ammonium compounds, which may increase the product shelf life in the dark; paraffin or similar wax-like substances, which may reduce oxygen inhibition during curing; amine stabilizers, which may consume dissolved oxygen during curing; and acrylated siloxanes, which may reduce the tackiness of the cured film.

According to various exemplary embodiments, the compositions of the disclosure do not comprise paraffins, wax-like substances, and/or amine stabilizers. In further exemplary embodiments, the compositions of the disclosure do not comprise acrylated siloxanes.

The composition of the disclosure may be formulated using any standard method known in the art. For example, the various components of the composition may be added singly or together to the formulation by stirring, blending, compounding, dry mixing, dissolution, suspension, and/or milling. The components may be added alone or as part of a mixture with solvents and/or other additives.

The compositions disclosed herein may be in any form suitable for application to a keratinous substrate. For example, the compositions may be in the form of a liquid, solution, or suspension. It is within the ability of a skilled artisan to select the type and amount of solvent, if present, depending on the type of composition and method of application. In certain embodiments, the solvent is inert, i.e., does not undergo a chemical reaction with the components of the composition. In other embodiments, the solvent should be able to be removed after coating the keratinous substrate. For example, the solvent may be removed by evaporation during the course of drying. Non-limiting examples of suitable solvents include ketones, alcohols, ethers, and esters. Useful solvents include acetone, ethyl acetate, butyl acetate, 2-methoxyethyl acetate, methyl ethyl ketone, methyl isobutyl ketone, methyl acetate, amyl acetate, and isopropyl acetate. The solvent may also comprise one or more diluents, such as saturated linear or branched hydrocarbons, for example, hexane and octane, or aromatic hydrocarbons, such as toluene and xylene, in a proportion generally ranging from about 10 to about 30 weight percent of the total weight of the liquid composition. Other volatile solvents may also be present in the solvent system, including ethanol, n-butanol, n-propanol, isopropanol, or mixtures thereof.

Systems and Methods

Also disclosed herein are systems and methods of treating, making up and/or enhancing the appearance of a keratinous substrate which comprise
(1) forming at least one film on the keratinous substrate by applying to the keratinous substrate a cosmetic composition comprising (a) at least one ethylenically unsaturated polymerizable compound and (b) at least one photoinitiator system comprising at least one photoinitiator having an absorption wavelength greater than about 350 nm, such as, for example, at least two photoinitiators wherein at least one photoinitiator has at least one absorption wavelength greater than about 350 nm, and optionally wherein the total amount of photoinitiators having at least one absorption wavelength greater than about 350 nm is greater than about 60% by weight, relative to the total weight of the photoinitiator system, and (2) exposing the film to UV-LED radiation. The photoinitiator system employed in the systems and methods of the disclosure may be chosen from any system described above with respect to the composition.

The film obtained according to the methods of the disclosure may, in certain embodiments, be relatively thin after curing, e.g., such films may have a thickness of less than about 15 mils (0.38 mm), such as less than about 10 mils (0.25 mm). For example, the films may have a thickness ranging from about 0.1 mil (0.002 mm) to about 10 mils, such as from about 0.5 mil (0.013 mm) to about 10 mils, or from about 1 mil (0.025 mm) to about 5 mils (0.13 mm), from about 0.002 mm to about 0.20 mm, from about 0.002 mm to about 0.15 mm, from about 0.013 mm to about 0.20 mm, or from about 0.013 mm to about 0.15 mm.

The composition may be applied to the keratinous substrate using any method known in the art. For example, in one embodiment, the composition may be brushed or sprayed onto the keratinous substrate. The composition may be applied to the keratinous substrate in the presence or absence of atmospheric oxygen. In various embodiments, the composition is applied in the presence of atmospheric oxygen, i.e., without the need for oxygen purging.

Furthermore, the systems and methods disclosed herein contemplate the application of more than one cosmetic composition to the keratinous substrate. For example, the systems and methods may comprise multilayer cosmetic applications, wherein various compositions according to the disclosure may be applied to the keratinous substrate multiple times and/or in varying sequences. In certain embodiments, a multilayer film may be formed on the keratinous substrate by application of (a) one or more base coats comprising a composition of this disclosure, (b) one or more intermediate coats comprising a composition of this disclosure, and (c) one or more top coats comprising a composition of this disclosure. The compositions in (a)-(c) may be identical or different, and may or may not comprise pigments and/or colorants. Each layer may optionally be exposed to UV-LED radiation after application to the keratinous substrate, and/or before application of additional layers. Other embodiments apparent to those skilled in the art are also intended to be encompassed by this disclosure.

According to various exemplary embodiments of the systems and methods disclosed herein, the film formed on the keratinous substrate is subsequently exposed to UV-LED radiation. In at least one exemplary embodiment, the film is exposed to radiation having a wavelength ranging from about 350 nm to about 450 nm, for instance, from about 380 nm to about 430 nm. In certain embodiments, the film may be exposed to visible light radiation having a wavelength greater than about 400 nm, for example, ranging from about 400 nm to about 800 nm.

In at least certain exemplary and non-limiting embodiments, the film may be exposed to radiation for a time period ranging up to about 10 minutes, for example, from about 5 seconds to about 7 minutes, from about 10 seconds to about 5 minutes, from about 20 seconds to about 2 minutes, or from about 30 seconds to about 1.5 minutes. In further exemplary embodiments, the film may be exposed to radiation for a time period ranging up to about one minute, for example from about 5 seconds to about one minute, such as about 10 seconds to about 40 seconds, or about 10 seconds to about 30 seconds. In systems and methods comprising the application of a multilayer film to the keratinous substrate, each layer may optionally be exposed to radiation for the time periods indicated above before application of additional layers.

One exemplary embodiment of the disclosure relates to systems and methods of making up and/or enhancing the appearance of a keratinous substrate which (1) form a film on a keratinous substrate by applying to said keratinous substrate a cosmetic composition comprising (a) at least one ethylenically unsaturated polymerizable compound and (b) at least one photoinitiator system comprising bis(2,4,6-trimethylbenzyol)-phenyl phosphine oxide and ethyl-2,4,6-trimethylbenzoylphenylphosphinate and (2) expose the film to UV-LED radiation.

Another exemplary embodiment of the disclosure relates to systems and methods of making up and/or enhancing the appearance of a keratinous substrate which (1) form a film on a keratinous substrate by applying to said keratinous substrate a cosmetic composition comprising (a) at least one ethylenically unsaturated polymerizable compound and (b) at least one photoinitiator system comprising bis(2,4,6-trimethylbenzyol)-phenyl phosphine oxide and/or ethyl-2,4,6-trimethylbenzoylphenylphosphinate and 1-hydroxy-cyclohexyl-phenyl-ketone and (2) expose the film to UV-LED radiation.

Yet another exemplary embodiment of the disclosure relates to systems and methods of making up and/or enhancing the appearance of a keratinous substrate which (1) form a film on a keratinous substrate by applying to said keratinous substrate a cosmetic composition comprising (a) at least one ethylenically unsaturated polymerizable compound and (b) at least one photoinitiator system comprising bis(2,4,6-trimethylbenzyol)-phenyl phosphine oxide and/or ethyl-2,4,6-trimethylbenzoylphenylphosphinate and 2-hydroxy-1-[4-(2-hydroxyethoxy)phenyl]-2-methyl-1-propanone and (2) expose the film to UV-LED radiation.

Yet a further embodiment relates to systems and methods of making up and/or enhancing the appearance of a keratinous substrate which (1) form a film on a keratinous substrate by applying to said keratinous substrate a cosmetic composition comprising (a) at least one ethylenically unsaturated polymerizable compound and (b) at least one photoinitiator system comprising bis(2,4,6-trimethylbenzyol)-phenyl phosphine oxide and/or ethyl-2,4,6-trimethylbenzoylphenylphosphinate and 2-hydroxy-2-methyl-1-phenyl-1-propanone and (2) expose the film to UV-LED radiation.

A still further exemplary embodiment relates to a process for forming a photocurable film on a keratinous substrate comprising applying to said keratinous substrate a cosmetic composition comprising (a) at least one ethylenically unsaturated polymerizable compound and (b) at least one photoinitiator system comprising at least two photoinitiators, wherein at least one photoinitiator has at least one absorption wavelength greater than about 350 nm and the total amount of photoinitiators having at least one absorption wavelength greater than about 350 nm is greater than about 60% by weight, relative to the total weight of the photoinitiator system.

Exemplary methods and processes contemplated according to the disclosure are intended for the treatment, make-up, coloring, and/or enhancement of keratinous substrates, such as the hair, skin, and nails. As such, the cosmetic compositions described herein include, but are not limited to, nail compositions (e.g., nail enamel and artificial nail compositions), make-up compositions (e.g., foundations and mascaras), sunscreen compositions, and hair-care compositions (e.g., hair-styling compositions). In at least one embodiment, the cosmetic composition is a nail composition. For example, the composition of the disclosure may be a gel-based nail enamel, artificial nail composition, or artificial nail extension, which may be applied to the fingernails and/or toenails.

It is to be understood that the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "an ethylenically unsaturated polymerizable compound" is intended to mean at least one ethylenically unsaturated polymerizable compound.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only.

Examples 1-42: Nail Enamels

Forty-two (42) nail compositions were prepared using the components listed in the following Tables 2 and 4. The components were added together to a container and mixed at room temperature. For each of the 42 compositions, the amounts of the ethylenically unsaturated polymerizable compounds remained constant, as indicated in Table 2, while the amount and/or composition of the photoinitiator system was modified, as indicated in Table 3. The amounts listed in Table 3 indicate the weight percent of each component relative to the total weight of the composition.

TABLE 2

Nail Compositions

| Component | Chemical Name | Amount (wt %) |
| --- | --- | --- |
| Ethylenically unsaturated polymerizable compound | Modified Epoxy Acrylate | 23% |
| Ethylenically unsaturated polymerizable compound | Polymeric Tetrafunctional Acrylate | 69.50% |
| Photoinitiator System | (Table 4) | (Table 3) |
| Solvent | Ethyl acetate | q.s. |

TABLE 3

Photoinitiator Systems

| | IRGACURE® 184 | DAROCUR® 1173 | IRGACURE® 2959 | IRGACURE® 819 | IRGACURE® 2100 | LUCIRIN® TPO-L |
|---|---|---|---|---|---|---|
| 1 | 0.5 | 0.5 | 1.5 | 0 | 1 | 1 |
| 2 | 1 | 1 | 0.5 | 0.5 | 2.5 | 0 |
| 3 | 0 | 2.5 | 0 | 0.5 | 1.5 | 1 |
| 4 | 2 | 1 | 0 | 0.5 | 1.5 | 0.5 |
| 5 | 0 | 3.5 | 0.5 | 0.5 | 0 | 2.5 |
| 6 | 3 | 0 | 0.5 | 1 | 1 | 0.5 |
| 7 | 1 | 0.5 | 3 | 0 | 3 | 0 |
| 8 | 0.5 | 0.5 | 3 | 0.5 | 1.5 | 1 |
| 9 | 1 | 0 | 0.5 | 0 | 0 | 1 |
| 10 | 2 | 1.5 | 0.5 | 1 | 0 | 2 |
| 11 | 0.5 | 0 | 3 | 0 | 1.5 | 1 |
| 12 | 0.5 | 3.5 | 0 | 0.5 | 1 | 2 |
| 13 | 0 | 0.5 | 0 | 3 | 0 | 2.5 |
| 14 | 0 | 0.5 | 0.5 | 1 | 4 | 0 |
| 15 | 0 | 0.5 | 2.5 | 3 | 1 | 0.5 |
| 16 | 0.5 | 1.5 | 0 | 1 | 0 | 4.5 |
| 17 | 0 | 1 | 0 | 1.5 | 3 | 1 |
| 18 | 0.5 | 1.5 | 0 | 1.5 | 0.5 | 3.5 |
| 19 | 1.5 | 0.5 | 0 | 1.5 | 1 | 2 |
| 20 | 0.5 | 0 | 2 | 0.5 | 1 | 3.5 |
| 21 | 3 | 0 | 0 | 2.5 | 0.5 | 1.5 |
| 22 | 0.5 | 0.5 | 1.5 | 1 | 3.5 | 0.5 |
| 23 | 2 | 0 | 0 | 1 | 1 | 2.5 |
| 24 | 2 | 0 | 1 | 2.5 | 2 | 0 |
| 25 | 0 | 0.5 | 0 | 3 | 0 | 1 |
| 26 | 0.5 | 1 | 0.5 | 0 | 3.5 | 0.5 |
| 27 | 1 | 0.5 | 1 | 3 | 1 | 0.5 |
| 28 | 0 | 2 | 0 | 0.5 | 4 | 0 |
| 29 | 0 | 0.5 | 0 | 1 | 4.5 | 0.5 |
| 30 | 1 | 1.5 | 0.5 | 0.5 | 3 | 1 |
| 31 | 1 | 2 | 0 | 2 | 0.5 | 2 |
| 32 | 1.5 | 0 | 0.5 | 0 | 4.5 | 1 |
| 33 | 0.5 | 0 | 0.5 | 2.5 | 0 | 2.5 |
| 34 | 0.5 | 0.5 | 1.5 | 2.5 | 2 | 0 |
| 35 | 0 | 0 | 1 | 3 | 2 | 1.5 |
| 36 | 1.5 | 0.5 | 1 | 0.5 | 2 | 2 |
| 37 | 0 | 0.5 | 1 | 1.5 | 1.5 | 0 |
| 38 | 1 | 1 | 0.5 | 3 | 1 | 0 |
| 39 | 0 | 3 | 0 | 0 | 3 | 1.5 |
| 40 | 0 | 0.5 | 0.5 | 1.5 | 0.5 | 0 |
| 41 | 1.5 | 0 | 0 | 2.5 | 1.5 | 1 |
| 42 | 1 | 0 | 0 | 2 | 0.5 | 0 |

The properties of each photoinitiator, including absorption wavelength data, are indicated in the following Table 4.

TABLE 4

Photoinitiator Properties

| Trade Name | Chemical Name | Absorption Wavelength(s) (nm) |
|---|---|---|
| IRGACURE 184® | 1-Hydroxy-cyclohexyl-phenyl-ketone | 230, 304 |
| IRGACURE® 2959 | 2-hydroxy-1-[4-(2-hydroxyethoxy)phenyl]-2-methyl-1-propanone | 276 |
| DAROCUR® 1173 | 2-hydroxy-2-methyl-1-phenyl-1-propanone | 245, 280, 331 |
| IRGACURE® 819 | bis(2,4,6-trimethylbenzyol)-phenyl phosphine oxide | 295, 370 |
| IRGACURE® 2100 | acylphosphine oxide mixture | 275, 370 |
| LUCIRIN® TPO-L | ethyl-2,4,6-trimethylbenzoylphenylphosphinate | 275, 295, 368, 380 |

IRGACURE® 184, IRGACURE® 2959, and DAROCUR® 1173 are α-hydroxyketone photoinitiators that do not have an absorption wavelength greater than about 350 nm. IRGACURE® 819 is a bisacylphosphine oxide (BAPO), LUCIRIN® TPO-L is a monoacylphosphine oxide (MAPO), and IRGACURE® 2100 is a mixture of MAPO and BAPO. IRGACURE® 819, LUCIRIN® TPO-L, and IRGACURE® 2100 each have at least one absorption wavelength greater than about 350 nm.

Compositions 1-42 were applied to a polymethyl methacrylate (PMMA) plate using a drawdown bar to produce a wet coating approximately 75 μm thick. The coatings were cured, without oxygen purging, using a Gelish Harmony 18G LED lamp for about 90 seconds. The films were evaluated for tackiness by touching the film with a finger and subsequently rated, where 0 indicates a tacky surface on which a fingerprint can be seen and 1 indicates a relatively non-tacky surface without any fingerprint. These observations are set forth in the following Table 5.

TABLE 5

Evaluation of Tackiness

| | Appearance | Observation Rating | Percentage of Photoinitiator With Absorption Wavelength >350 nm |
|---|---|---|---|
| 1 | clear | 0 | 44.44% |
| 2 | clear | 0 | 54.55% |

TABLE 5-continued

Evaluation of Tackiness

| | Appearance | Observation Rating | Percentage of Photoinitiator With Absorption Wavelength >350 nm |
|---|---|---|---|
| 3 | clear | 0 | 54.55% |
| 4 | clear | 0 | 45.45% |
| 5 | clear | 0 | 42.86% |
| 6 | clear | 0 | 41.67% |
| 7 | clear | 0 | 40.00% |
| 8 | clear | 0 | 42.86% |
| 9 | clear | 0 | 40.00% |
| 10 | clear | 0 | 42.86% |
| 11 | clear | 0 | 41.67% |
| 12 | clear | 0 | 46.67% |
| 13 | clear | 1 | 91.67% |
| 14 | clear | 1 | 83.33% |
| 15 | clear | 1 | 60.00% |
| 16 | clear | 1 | 73.33% |
| 17 | clear | 1 | 84.62% |
| 18 | clear | 1 | 73.33% |
| 19 | clear | 1 | 69.23% |
| 20 | clear | 1 | 66.67% |
| 21 | clear | 1 | 60.00% |
| 22 | clear | 1 | 66.67% |
| 23 | clear | 1 | 69.23% |
| 24 | clear | 1 | 60.00% |
| 25 | clear | 1 | 88.89% |
| 26 | clear | 1 | 66.67% |
| 27 | clear | 1 | 64.29% |
| 28 | clear | 1 | 69.23% |
| 29 | clear | 1 | 92.31% |
| 30 | clear | 1 | 60.00% |
| 31 | clear | 1 | 60.00% |
| 32 | clear | 1 | 73.33% |
| 33 | clear | 1 | 83.33% |
| 34 | clear | 1 | 64.29% |
| 35 | clear | 1 | 86.67% |
| 36 | clear | 1 | 60.00% |
| 37 | clear | 1 | 66.67% |
| 38 | clear | 1 | 61.54% |
| 39 | clear | 1 | 60.00% |
| 40 | clear | 1 | 66.67% |
| 41 | clear | 1 | 76.92% |
| 42 | clear | 1 | 71.43% |

As shown in Table 5 above, compositions comprising a photoinitiator system comprising less than about 60% by weight of photoinitiators having at least one absorption wavelength greater than about 350 nm (compositions 1-12) produced films with tacky surfaces upon curing with UV-LED radiation. In contrast, compositions in accordance with the present disclosure in which the photoinitiator system comprises greater than about 60% by weight of photoinitiators having at least one absorption wavelength greater than about 350 nm (compositions 13-42) produced relatively tack-free films upon curing with UV-LED.

What is claimed is:

1. A cosmetic composition comprising:
   (a) at least one ethylenically unsaturated polymerizable compound, and
   (b) at least one photoinitiator system comprising at least two photoinitiators,
   wherein at least one first photoinitiator has at least one absorption wavelength greater than about 350 nm,
   wherein at least one second photoinitiator does not have an absorption wavelength greater than about 350 nm,
   wherein the at least one first photoinitiator is present in an amount ranging from about 1% to about 7% by weight, relative to the total weight of the composition, and
   wherein the total amount of photoinitiators having at least one absorption wavelength greater than about 350 nm is greater than about 60% by weight, relative to the total weight of the photoinitiator system.

2. The cosmetic composition of claim 1, wherein the at least one ethylenically unsaturated polymerizable compound is chosen from mono-, di-, tri-, and poly-functional (meth)acrylic monomers; urethane (meth)acrylates; acrylated polyester oligomers; acrylated polyether oligomers; and acrylated acrylate oligomers.

3. The cosmetic composition of claim 1, wherein the at least one ethylenically unsaturated polymerizable compound is present in the composition in an amount ranging from about 10% to about 90% by weight, relative to the total weight of the composition.

4. The cosmetic composition of claim 1, wherein the at least one first photoinitiator having at least one absorption wavelength greater than about 350 nm is chosen from monoacylphosphine oxides and bisacylphoshpine oxides.

5. The cosmetic composition of claim 4, wherein the at least one first photoinitiator is chosen from bis(2,4,6-trimethylbenzyol)-phenyl phosphine oxide and ethyl-2,4,6-trimethylbenzoylphenylphosphinate.

6. The cosmetic composition of claim 1, wherein the at least one second photoinitiator is chosen from α-hydroxyketones; α-aminoketones; benzophenones; ketal compounds; monomeric and dimeric phenylglyoxylic acids and esters thereof; and oxime esters.

7. The cosmetic composition of claim 6, wherein the at least one second photoinitiator is chosen from 1-hydroxycyclohexylphenylketone, 2-hydroxy-1-[4-(2-hydroxyethoxy)phenyl]-2-methyl-1-propanone, and 2-hydroxy-2-methyl-1-phenyl-1-propanone.

8. The cosmetic composition of claim 1, wherein the total amount of photoinitiators having at least one absorption wavelength greater than about 350 nm is greater than about 65% by weight, relative to the total weight of the photoinitiator system.

9. The cosmetic composition of claim 1, chosen from gel-based nail enamel compositions and artificial nail compositions.

10. The cosmetic composition of claim 1, further comprising at least one additional component chosen from binders, film formers, pigments, and solvents.

11. A method of treating, making up, and/or enhancing the appearance of a keratinous substrate comprising:
   (1) forming a film on the keratinous substrate by applying to said keratinous substrate a composition comprising:
      (a) at least one ethylenically unsaturated polymerizable compound, and
      (b) at least one photoinitiator system comprising at least two photoinitiators,
      wherein at least one first photoinitiator has at least one absorption wavelength greater than about 350 nm,
      wherein at least one second photoinitiator does not have an absorption wavelength greater than about 350 nm,
      wherein the at least one first photoinitiator is present in an amount ranging from about 1% to about 7% by weight, relative to the total weight of the composition, and
      wherein the total amount of photoinitiators having at least one absorption wavelength greater than about 350 nm is greater than about 60% by weight, relative to the total weight of the photoinitiator system, and
   (2) exposing the film to UV-LED radiation.

12. The method of claim 11, wherein the keratinous substrate is chosen from fingernails and toenails.

13. The method of claim 11, wherein the cosmetic composition is a nail composition chosen from gel-based nail enamel compositions and artificial nail compositions.

14. The method of claim 11, wherein the film has a thickness of less than about 0.25 mm.

15. The method of claim 11, wherein the at least one ethylenically unsaturated polymerizable compound is chosen from mono-, di-, tri-, and poly-functional (meth)acrylic monomers; urethane (meth)acrylates; acrylated polyester oligomers; acrylated polyether oligomers; and acrylated acrylate oligomers.

16. The method of claim 11, wherein the at least one first photoinitiator having at least one absorption wavelength greater than about 350 nm is chosen from monoacylphosphine oxides and bisacylphoshpine oxides.

17. The method of claim 11, wherein the at least one second photoinitiator is chosen from α-hydroxyketones; α-aminoketones; benzophenones; ketal compounds; monomeric and dimeric phenylglyoxylic acids and esters thereof; and oxime esters.

18. The method of claim 11, wherein the total amount of photoinitiators having at least one absorption wavelength greater than about 350 nm is greater than about 70% by weight, relative to the total weight of the photoinitiator system.

19. The method of claim 11, wherein the film is exposed to radiation having a wavelength ranging from about 350 nm to about 450 nm.

20. The method of claim 11, wherein the film is exposed to radiation for a time period ranging from about 10 seconds to about 5 minutes.

21. A process for forming a photo-curable film on a keratinous substrate, said process comprising applying to the keratinous substrate a composition comprising:
   (a) at least one ethylenically unsaturated polymerizable compound, and
   (b) at least one photoinitiator system comprising at least two photoinitiators,
   wherein at least one first photoinitiator has at least one absorption wavelength greater than about 350 nm,
   wherein at least one second photoinitiator does not have an absorption wavelength greater than about 350 nm,
   wherein the at least one first photoinitiator is present in an amount ranging from about 1% to about 7% by weight, relative to the total weight of the composition, and
   wherein the total amount of photoinitiators having at least one absorption wavelength greater than about 350 nm is greater than about 60% by weight, relative to the total weight of the photoinitiator system.

\* \* \* \* \*